United States Patent [19]
Myers

[11] Patent Number: 5,891,845
[45] Date of Patent: Apr. 6, 1999

[54] DRUG DELIVERY SYSTEMS UTILIZING LIQUID CRYSTAL STRUCTURES

[75] Inventor: Garry Myers, Kingsport, Tenn.

[73] Assignee: Fuisz Technologies Ltd., Chantilly, Va.

[21] Appl. No.: 975,827

[22] Filed: Nov. 21, 1997

[51] Int. Cl.⁶ .......................... A61K 38/13; A61K 31/55; A61K 31/44; A61K 9/48
[52] U.S. Cl. ............................. 514/11; 514/211; 514/356; 424/452; 424/455
[58] Field of Search ..................................... 514/211, 356; 424/452, 455

[56] References Cited

U.S. PATENT DOCUMENTS

| | | | |
|---|---|---|---|
| 3,867,521 | 2/1975 | Miskel et al. | 424/37 |
| 4,944,949 | 7/1990 | Story et al. | 424/451 |
| 5,342,625 | 8/1994 | Hauer et al. | 424/455 |
| 5,430,017 | 7/1995 | Antalne et al. | 514/9 |
| 5,583,105 | 12/1996 | Kovacs et al. | 514/11 |

FOREIGN PATENT DOCUMENTS

0712631 A2  5/1996  European Pat. Off. .

OTHER PUBLICATIONS

Sheu et al, Derwent Drug File Abstracts, abstract No. 96–18846, 1995.
Wu et al, Derwent Drug File Abstracts, abstract No. 95–05631, 1994.
Chi et al, Derwent Drug File Abstracts, abstract No. 96–20886, 1995.
MSDS Brochure: "Eastman Vitamin E TPGS (d–Alpha–Tocopheryl Polyethylene Glycol 1000 Succinate)", 1994.
Valantine et al., Recent Advances in Cardiac Transplantation, N. Engl. J. Med. 1995; vol. 333, No. 10, pp. 660–661.
Sokol et al., Improvement of Cyclosporin Absorption in Children After Liver Transplantation by Means of Water–Soluble Vitamin E, The Lancet, vol. 338: Jul. 27, 1991, pp. 212–215.
Robbins et al., Safe Coadministration of Terbinafine and Terfenadine: a Placebo–Controlled Crossover Study of Pharmacokinetic and Pharmacodynamic Interactions in Healthy Volunteers, Clinical Pharmacology & Therapeutics, vol. 59, No.3(Mar. 1996), pp. 275–283.

*Primary Examiner*—William R. A. Jarvis

[57] ABSTRACT

Vitamin E TPGS/drug compositions and methods are provided which obviate the need for surfactants or non-evaporated co-solvents because the active drug component is dissolved directly into Vitamin E TPGS to form a true molecular solution—not an emulsion or a micro-emulsion. The invention provides a slowly dissolving TPGS/Drug matrix that absorbs gastrointestinal fluid into the matrix at the dosage form/fluid interface, where a gel-like liquid crystal is formed. This gel front forms a liquid crystal boundary where drug dissolution is highest. At this liquid crystal/GI fluid boundary, a synchronization takes place in which the rate of formation of liquid crystals equals the dissolution rate of liquid crystals at the water interface, thereby giving controlled order release of the drug into the GI tract. The rate of dissolution is also controlled by the geometry of the dosage form. The solid Vitamin E TPGS/drug matrices of the invention can be solidified and compressed into tablets or filled into capsules, with other excipients, binders and/or fillers. The solid TPGS/drug solution of the invention also can be made into an immediate release liquid formulation upon addition of water, or into a controlled release system solid tablet by the use of impermeable or semi-permeable barriers or coatings surrounding portions of the tablet.

41 Claims, 1 Drawing Sheet

DRUG DELIVERY SYSTEMS UTILIZING LIQUID CRYSTAL STRUCTURES

I. FIELD OF THE INVENTION

This invention relates to the field of pharmaceutical drug compositions and delivery devices, and particularly to the use of substances and devices that form liquid crystal structures to enhance the solubility and control the release of active drug compounds in the patient. The present invention solves solubility and toxic side effect problems associated with prior art immediate release formulations of certain highly insoluble drugs, e.g., cyclosporine. In particular, the present invention utilizes the ability of Vitamin E TPGS to form liquid crystal structures with gastric fluid to enhance drug solubility, and further employs dosage forms with impermeable or semi-permeable barriers to control drug release over time, thereby providing a means for lowering dose within the therapeutic window.

II. BACKGROUND OF THE INVENTION

A. Technical Background.
1. Drugs.

A drug is broadly defined as a chemical agent or medicinal substance that therapeutically affects the living processes of a patient. To perform its characteristic therapeutic activity, a therapeutic amount of a drug compound must be made bioavailable, i.e., it must be able to get to its site of action in the patient, via the blood stream, in the case of an oral or parenteral drug formulation. With respect to oral drug formulations (e.g., tablets, caplets, and capsules), a therapeutic amount of the drug must be first released from the dosage form over a given time in the gut, and, must be solubilized and absorbed in the gastrointestinal tract. After absorption, the active drug compound is metabolized, passes through the liver, and then it (and/or one or more of its metabolites) enters the general circulatory system towards the site of action. Thus, proper drug release from the dosage form, and solubilization of the active drug compound in the GI tract, are the critical first steps in the development of oral drug therapies.

The present invention relates to drug delivery systems that utilize liquid crystal structures and other means to dissolve and control the rate of dissolution of drug compounds, e.g., cyclosporine and nifedipine, that are poorly soluble in the gastrointestinal tract.

Medicinal substances which can be used in the present invention are varied and include, but are not limited to, antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodilators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, anti-obesity drugs, anabolic drugs, erythropoietic drugs, anti-asthmatics, cough suppressants, mucolytics, anti-uricemic drugs and mixtures thereof. Popular $H_2$-antagonists which are contemplated for use in the present invention include cimetidine, ranitidine hydrochloride, famotidine, nizatidine, ebrotidine, mifentdine, roxatidine, pisatidine and aceroxatidine. Analgesics include aspirin, acetaminophen, and acetaminophen plus caffeine, Ibuprofen. Other preferred active drugs for use in this invention include anti-diarrheals such as immodium AD. Also contemplated for use herein are anxiolytics such as Xanax; antipsychotics such as clozaril and Haldol; non-steroidal anti-inflammatories (NSAIDs) such as Voltaren and Lodine; anti-histamines such as terfenadine, Hismanal, Relafen, and Tavist; antiemtics such as Kytril and Cesamet; bronchodilators such as Bentolin, Proventil; antidepressants such as Prozac, Zoloft, Paxil and Buspar; antimigraines such as Imigran, ACE-inhibitors such as Vasotec, Capoten and Zestril; Anti-Alzheimers agents, such as Nicergoline; and $Ca^H$-Antagonists such as Procardia, Adalat, and Calan, and salts thereof.

Especially preferred drugs for use in this invention are the immunosuppressants, e.g., the cyclosporins, and calcium antagonists, e.g., nifedipine and Ditiazem HCL. As discussed below, the present invention can be used for both hydrophilic and lipophilic drugs.

2. Cyclosporine, Nifedipine and Diltiazem.HCl.

The cyclosporins comprise class of structurally distinctive, cyclic, poly-N-methylated endecapeptides, possessing pharmacological activity, including, immunosuppressive, anti-inflammatory and/or anti-parasitic activity. Cyclosporine, also known as Cyclosporin A (see chemical structure shown below), was one of the first Cyclosporins to be isolated. See U.S. Pat. No. 5,342,625 to Birgit et al. Cyclosporine is a cyclic polypeptide immunosuppressant agent consisting of 11 amino acids, and is produced in nature as a metabolite by the fungus species *Beauveria nivea*. See PHYSICIAN'S DESK REFERENCE, $51^{st}$ Ed. (1997), p. 2405.

The chemical structure of cyclosporine is:

The present invention is intended to cover compositions of and methods employing the use of the cyclosporin class, which can be described as a group of nonpolar cyclic oligopeptides with immunosuppresant activity. This include Cyclosporins A, B, C, D and G. Cyclosporins are practically water-insoluble substances formed from neutral, hydrophobic amino acids. As a consequence of their high molecular weight (over 1000), poor water solubility, the cyclosporins are absorbed only to an insignificant extent from the gastrointestinal tract when administered orally. See U.S. Pat. No. 5,430,017 to Antalné et al. After oral administration, the bioavailability of cyclosporine or cyclosporin A is markedly poor and variable due to factors that include its poor solubility in aqueous gastrointestinal fluids, its high lipophilicity, as well as other factors such as impaired bile flow and fat content in the diet. See Chang et al., *Clinical Pharmacology & Therapeutics*, Vol. 59, No. 3 (March 1996).

Cyclosporine dosing is variable and depends on the type of organ transplanted. Generally, it about 7, 8 and 9 mg/kg of body weight, divided into two doses, for the heart, liver, renal (kidney), respectively. Cyclosporine has a biphasic terminal half-life of about 8.4 hours. Cyclosporine forms a solid solution with Vitamin E TPGS.

Nifedipine, or 3,5-pyridinecarboxylic acid, 1,4-dihydro-2,6-dimethyl-4-(2-nitrophenyl)-, dimethyl ester (see chemical structure shown below), is a potent peripheral vasodilator. About 90% of an oral dose of nifedipine is absorbed, but its bioavailability is 65% to 70%, and there is significant first pass metabolism. Greater than 10% of the drug is bound to plasma protein, and is metabolized to inactive metabolites, probably by the liver. Most of the inactive metabolites are excreted. The half-life is two to six hours.

The chemical structure of nifedipine is:

Nifedipine is practically insoluble in water. Its current dosage forms include 10 and 20 mg capsules. It is dosed three to four times a day, and doses exceeding 180 mg a day are not recommended. Nifedipine side effects of overdosing include pronounced hypotension requiring cardiovascular support.

For these reasons, Nifedipine is a good candidate for both enhanced solubility systems, and/or for use in a controlled release device which can effectively deliver a one to two per day dose. Nifedipine forms a solid solution with Vitamin E TPGS.

Diltiazem Hydrochloride, or benzothiazepin-4(5H)-one, 3-(acetyloxy)-5[2-(dimethylamino)ethyl]-2,3dihydro-2(4-methoxyphenyl)-, (+)-cis-, monohydrochloride (see chemical structure below), is a potent coronary vasodilator. Diltiazem-HCl is freely soluble in water. It is 80% absorbed orally, but only 40 to 60% of an oral dose reaches the systemic circulation because of first-pass metabolism.

The chemical structure of diltiazem hydrochloride is:

Diltiazem.HCl is metabolized extensively to several metabolites, some of which have weak coronary vasodilator activity. Less than 4% of the drug appears unchanged in the urine, and plasma half-life is about 4 hours. Diltiazem may reach saturation kinetics after single doses of greater than 60 mg. For these reasons, it is desirable to provide a one to two per day controlled release form of diltiazem hydrochloride. Diltiazem side effects include hypotension, itching, burning, flushing, arrythmia, and atrail flutter. Diltiazem forms a solid dispersion with Vitamin E TPGS.

3. Drug Formulations.

Once pharmacologic activity for a drug compound becomes known, the next objectives are to design drug product systems and/or devices that will effectively and efficiently deliver the compound to its active site. Moreover, after a system is developed and used, skilled drug formulators will often seek to improve or completely re-design it with the goal of optimizing drug delivery.

Broadly speaking, drug delivery systems include those that deliver the active drug compound by topical, aerosol, oral, injectable or rectal means. The oral dosage forms include tablets, capsules, gel capsules, syrups, suspensions, emulsions, micro-emulsions, pre-emulsion concentrates, and similar systems.

The development of an oral dosage form for an active drug is often driven by solubility concerns. The drug formulation, i.e., the combining of the active drug compound together with other inactive compounds and ingredients, will affect the amount or concentration of the drug compound that gets to the active site over the course of a given time period. The composition of the drug formulation directly affects the solubilization of the drug compound in the gastrointestinal tract, and consequently the extent and rate of the absorption of the active drug compound into the blood stream. In addition, the therapeutic value of a drug is also affected by the rate in which the drug dose is released from the delivery system itself, which in turn affects the rate and extent of solubilization of the active compound in the gastrointestinal tract prior to absorption.

The formulation of an acceptable dosage form for the delivery of a drug compound to the active site in the human body is a complex process involving trial and error. The development of an oral formulation for an insoluble or poorly soluble drug often involves the designing of a system that will affect the pH of the micro-environment surrounding the drug form in the gastrointestinal tract after ingestion.

In particular, the formulation may contain disintegrants and/or other agents that work to increase or decrease the pH of the micro- environment, and thus enhance drug dissolution. In addition, the drug may also be granulated to reduce its particle size and/or increase the surface area that is exposed to the gastric fluid. The amount of exposed surface area will affect the rate of drug dissolution and thus the amount of active drug that will be absorbed by the patient.

With respect to drug compounds of very poor or limited solubility, like cyclosporine, skilled formulators have used co-solvents, surfactants or wetting agents to reduce the surface tension of the liquid environment of the gastric fluid in which the active drug is to be dissolved. These agents wet the active drug more quickly so that more of the drug is exposed to the gastric fluid in a shorter time, and may enhance its dissolution. Common types of surfactants and co-solvents that can be used include the cationic, anionic (e.g., sodium lauryl sulfate and gelatin), and nonionic (e.g., MYRG) types, as well as such co-solvents as the polyethylene glycols ("PEGs").

The role of the binder in the tablet drug form is to provide a tablet with sufficient hardness and integrity, but also must allow for sufficient disintegration and dissolution in the gastric environment. In this sense, a binder performs the opposite function of a disintegrant. The types of binders that can be used in drug formulations include gelatins of numerous grades, starches and starch derivatives (including corn starch, StaRx 1500, carboxymethylated starch), cellulose derivatives, polyvinylpyrollidones, Veegums, polyethylene glycols, sugars, e.g., sucrose and lactose, sodium alginate and waxes.

The fillers used to bulk up a drug tablet or other form also should not interfere with the tablet's dissolution. Numerous fillers include the starch derivatives, sugars (e.g., lactose and sucrose), sorbitol, mannitol, cellulose derivatives and their inorganic salts, corn starch, Starch 1500, calcium phosphate, and Avicel.

Likewise, lubricants aid in the machining of a drug tablet. Every tablet needs a lubricant so that it will be ejected from the machine die with minimum force. However, the lubricant also must not interfere with the dissolution of the tablet. Lubricants include waxes, fatty acids, sodium salts of fatty acids and stearates.

4. Controlled Release Drug Formulations.

Controlled release formulations employ means that allow less drug to be released into the gut over time, and thereby allow the body to see lower concentrations of drug per unit time. They can thereby provide continuous delivery of the drug for a predetermined period, with predictable and reproducible kinetics. The term "controlled release" also refers to systems that provide control over the movement of the dosage form through the gastrointestinal tract, or that deliver the drug to a specific area for either local or systemic effect. See, generally, Gupta and Robinson, TREATISE ON ORAL CONTROLLED-DRUG DELIVERY [Text Ed. 1992], Ch. 6, edited by Agis Kydonieus, Mancel Dekker, Inc. ISBN 0-8247-8519-3.

Generally, there are three categories of oral drug delivery systems: conventional or immediate, first order slow release, and zero order release. In the conventional dosage form, a large maximum/minimum plasma drug concentration (Cmax/Cmin) is typically observed due to a rapid absorption of the drug into the body, relative to the drug's therapeutic index, i.e., the ratio of the maximum drug concentration needed to produce and maintain a desirable pharmacological response. In the conventional systems, drug content is released into the gastrointestinal tract within a short period of time, and plasma drug levels peak at a given time, usually within a few hours after dosing. The design of conventional oral drug delivery systems, including the cyclosporine formulations of the prior art, is generally based on getting the fastest possible rate of drug dissolution, often at the risk of creating undesirable, dose related side effects.

The goal of a controlled release formulation is to improve the therapeutic value of the active drug component by reducing the ratio of the maximum and minimum plasma drug combination (Cmax/Cmin) while maintaining drug plasma levels within the therapeutic window. The controlled release form seeks to give a drug with sufficient frequency and dose so that the ratio Cmax/Cmin in plasma at steady state is less than the therapeutic index, and to maintain drug levels at constant effective concentrations. In principle, in order to keep a constant plasma drug level, the drug formulation should be designed to provide an input rate into the body that is or approaches zero order, although in vivo profiles rarely match zero order kinetics based on in vitro models. The dosage forms of the present invention can be constructed along zero order, first order, or conventional release systems.

The type of controlled release systems that involve continuous or controlled release of the active drug employ dissolution control, diffusion control, a combination of dissolution and diffusion control, ion-exchange resins, osmotically controlled devices, slow dissolving salts or complexes, and pH independent formulations. These systems include tablet or similar formulations impregnated with water insoluble waxes, such as fatty acids, carnuba wax, and bees wax, or polymers, such as polyethylene, polypropylene, methacrylates, silicones, and PVC. When gastric fluid penetrates the surface of a polymer-impregnated tablet, the drug dissolves and diffuses through the polymer network. Other systems in these categories employ the encapsulation or microencapsulation of the drug particles with a slowly dissolving material prior to tablet compression. See Gupta and Robinson, supra; EUDRAGIT brochure: "EUDRAGIT Powders for Direct Compression," Hüls America Inc, Somerset, N.J.; and UNION CARBIDE brochure: "SENTRY POLYOX, Water-Soluble Resins, NF In Sustained-Release Oral Pharmaceutical Applications," Union Carbide, Danbury Conn. (1995).

Other controlled release formulations are comprised of hydrophillic systems wherein a preparation of hydrophilic polymers, such as hydroxy propyl methyl cellulose, methyl cellulose, sodium carboxy methyl cellulose, polyethylene oxide polymers, natural gums and starches, is dispersed together with the drug and other excipients. These hydrophillic systems work by the uptake of the gastric fluid by the polymer, which is followed by swelling, dissolution of the drug, and diffusion through the swollen complex. Alternatively, they may work by the swelling of the complex and then erosion or dissolution of the polymer complex. See Gupta and Robinson, supra.

Generally, controlled delivery of lipophilic drugs requires techniques different than those employed with hydrophilic drugs. Lipophilic drugs must be solubilized and are, preferably, released in a controlled fashion, whereas hydrophilic drugs tend naturally to increase the rate at which water absorption and drug diffusion occurs. Consequently, a hydrophilic drug form must be modified to slow down the delivery.

Figure 3:
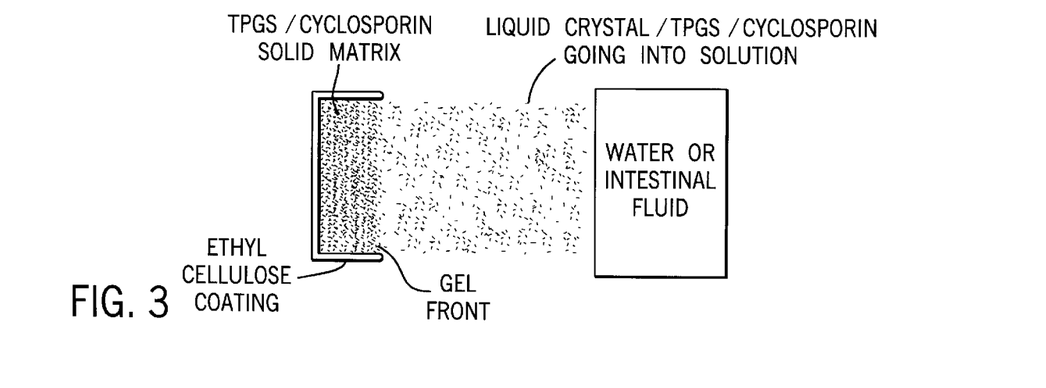
FIG. 3 depicts a drug/TPGS dose form undergoing erosion over time at the liquid crystal/gastrointestinal fluid interface.

The present invention, however, does not depend on the lipophilicity or hydrophilicity of the drug component because it functions by gradual surface dissolution of liquid crystal structures. As discussed below, the Vitamin E TPGS component of formulations within the scope of the present invention serves not only to solubilize lipophilic drugs and to disperse hydrophilic drugs, but also establishes a viscous liquid crystal gel structure at the dosage form/water interface, at which the dosage form slowly erodes as it goes into solution. See e.g. FIG. [3]. Thus, controlled diffusion of both hydrophilic and lipophilic drugs formulated in accordance with the present invention can be achieved.

In general, the advantages of controlled release systems may include reduced dosing frequency, better patient convenience and compliance, reduced gastrointestinal side effects and/or toxic side effects, fewer fluctuating plasma drug levels, more uniform drug effect, and lesser total dose.

It is particularly desirable to employ a controlled release system for cyclosporine as an alternative to the immediate release cyclosporine drug products of the prior art, e.g., NEORAL and SANDIMMUNE. The prior art cyclosporine products can result in toxic side effects, including nephrotoxic effects, due to the rapid release and absorption of high blood concentrations of the drug. See PHYSICIAN'S DESK REFERENCE, $51^{st}$ Ed. (1997), p. 2405 (black box warning). Nephrotoxicity is believed to be a serious side effect caused by cyclosporine, and is dose related. When the dose is reduced, or another immunosuppressive agent is substituted, renal function improves. See e.g., Valantine H A, Shroeder I S, N. Engl. J. Med. 1995; 333: 660–661.

In an effort to reduce the nephrotoxic risks associated with cyclosporine therapy, prior art investigators have co-administered the drug with an agent that delays the metabolism of cyclosporine, effectively extending the half life and reducing the dose required to maintain therapeutic blood levels. However, this invention seeks to achieve these goals by providing a novel controlled release drug delivery system that does not require the co-administration of other agents. The present invention can control and reduce the release of cyclosporine per unit time, making it less than that of the immediate release formulation of the prior art. Thus, the present invention, unlike the prior art, does not overload the kidneys with immediate high levels of cyclosporine, thereby reducing the risks of nephrotoxicity.

5. Vitamin E TPGS.

In recent years, Vitamin E TPGS, or d-α-tocopheryl polyethylene glycol 1000 succinate, has been used as one of many excipients in complex immediate release drug formulations, usually emulsions or micro-emulsions, wherein the active drug compound is poorly soluble in water.

Vitamin E TPGS is a water soluble derivative of natural source Vitamin E, and has a dual nature, similar to an amphiphile, of hydrophilicity and lipophilicity. TPGS is also believed to be a bioavailability enhancer when co-administered with some lipophilic drugs, including cyclosporine.

The structure of the principal component of TPGS is:

Vitamin E TPGS is miscible in water and forms solutions with water at concentrations up to approximately 20% wt, beyond which liquid crystalline phases may form. It has a melting point of about 38° to 41° C. (100° to 106° F.). See, generally, "Eastman Vitamin E TPGS" Eastman Brochure, Eastman Chemical Co., Kingsport, Tenn. (October 1996). It has a relatively high crystallinity, high degradation temperature, and good thermal stability.

TPGS forms liquid crystalline phases in water. Micelles are formed at 0.02 percent weight. When TPGS concentration is above 20 percent weight, higher-viscosity liquid crystalline phases start to form. With increasing TPGS concentration in water, more complex liquid crystalline phases evolve, e.g., from isotropic globular micellar, to isotropic cylindrical micellar and hexagonal, hexagonal, mixed hexagonal and reversed hexagonal, reversed globular micellar, and to the lamellar phase. See "Eastman Vitamin E TPGS" Eastman Brochure, Eastman Chemical Co., Kingsport, Tenn. (October 1996).

TPGS is known as a surface active agent or as an emulsifier for use in complex formulations that include a number of other excipients that function as solvent, binder, and filler. However, the inventor herein knows of no examples wherein TPGS is used as the only or major solvent in a drug formulation, or as the delivery vehicle for controlled release of drugs, performing all of the functions of solvent, surfactant, binder, filler, and liquid crystal gel former. The Eastman Brochure, supra, suggests the blending of TPGS with water and a lipophilic drug to form an oil in water emulsion, but does not teach or suggest the direct melt blending, or solvent evaporation, of a lipophilic drug, such as cyclosporine, or dispersion of hydrophilic drugs, e.g., Diltiazem.HCl Salt, and TPGS, to form a solid solution or dispersion of drug and TPGS. (See Hawley's Condensed Chemical Dictionary (1987) for a definition of "dispersion"). Nor does the prior art teach or suggest the dry blending or mechanical mixing and compression of a solid solution of drug and Vitamin E TPGS for tablets, capsules or powder forms of drug/TPGS formulations where the drug is in a true Vitamin E TPGS solution, or solid dispersion, as opposed to an emulsion. The prior art also fails to disclose or teach the art of controlling the release or dissolution of the active drug form through the use of TPGS liquid crystal formation. Nor does the prior art teach the controlled dissolution at the surface of an oral dosage form, using liquid crystal formation of TPGS with water as the control mechanism.

B. The Prior Art.

Generally, attempts to formulate cyclosporine for use in aqueous environments, including human and other mammal gastrointestinal fluid, include the use of formulations consisting of oil-in-water or water-in-oil emulsions and micro-emulsion pre-concentrates with cyclosporine as the active ingredient. As discussed below, the use of Vitamin E TPGS in the prior art has been limited to concomitant administration, or co-administration, of the drug and Vitamin E, or, to the use of TPGS together with other solvents, co-solvents, surfactants, and/or other solubility enhancers in an emulsion or micro-emulsion environment.

By contrast, the drug compositions of the present invention are formed from true solutions (not emulsions or micro-emulsions), comprising appropriate ratios of drug/Vitamin E TPGS, that do not require the presence or absence of emulsifiers, co-solvents, surfactants, or other solubility agents in order to maintain the drug in solution. The prior art has failed to utilize or teach the liquid crystal forming nature of Vitamin E TPGS to create true drug/liquid crystal solid or liquid solutions that, when properly constructed, will result in either immediate release or controlled release drug delivery systems.

The emulsion and micro-emulsion cyclosporine formulations of the prior art suffer numerous disadvantages. They employ highly complex systems that provide generally immediate release formulations that disperse quickly in the gastrointestinal tract, thereby permitting the amount of dissolved cyclosporine to be rapidly absorbed and taken into the blood stream at once. The prior art formulations create the risk of side effects by allowing toxic blood levels of cyclosporine to be established in the body. In addition, they require the use of ethanol and other undesirable solvents, and are not easily made into convenient hard tablets or caplets.

For example, Hauer et al., U.S. Pat. No. 5,342,625, and commercial cyclosporine formulations, such as those sold under the trade marks SANDIMMUNE and NEORAL, disclose emulsions and pre-emulsion forms of cyclosporine. These products consist of soft gelatin capsules and oral solutions containing a cyclosporin in an emulsion or micro-emulsion pre-concentrate that forms a micro-emulsion in aqueous media, and seek to achieve immediate release and absorption of the drug. The Hauer et al. cyclosporine formulations are characterized by a high alcohol content, and emulsify the drug by using numerous additional solvents, co-solvents and surfactants such as corn oilmono-ditriglycerides, poly-oxyl 40 hydrogenated castor oil NF, DL-α-tocopherol USP, and gelatin NF.

These and other prior art cyclosporine emulsion or microemulsion compositions employ complex hydrophilic phase components, consisting of complex ethers, and lipophilic phase components, consisting of medium chain fatty acid triglycerides, including neutral oils such as fractionated coconut oils. They also require surfactants, such as the reaction products of vegetable oils and ethylene glycol, polyoxyethylene-sorbitan-fatty acid esters, e.g., TWEEN 40 and TWEEN 80, and polyoxyethylene-polyoxyproplylene co-polymers, and phospholipids, and thickening agents such as polyacrylate and polyacrylate co-polymer resins, celluloses and cellulose derivatives, polyvinyl pyrrolidones, polyvinyl resins, and inorganic thickening agents, such as atapulgite, bentonite, and silica gels.

The attempts to improve the emulsion and microemulsion formulations of Hauer et al., SANDIMMUNE and NEORAL simply add more co-solvents and surfactants to what are already overly complex systems.

U.S. Pat. No. 5,430,017 to Antalné et al., discloses a liquid pharmaceutical solution wherein a cyclosporin is dissolved in the mixture of propylene glycol and a polyoxyethylene/polyoxyproplyene block polymer, optionally in the presence of ethanol. The Antalné et al. mixture is said to result in a solution that, after combination with water or fruit juices, precipitates the cyclosporin in the form of finely dispersed particles, which in turn is said to be rapidly absorbed from the gastrointestinal tract due to the large surface area of the particles of the active ingredient and the effect of the block polymer.

Similarly, European Application No. EP 0712 631 A2 to Kovacs et al. Discloses a cyclosporine containing multiple emulsion pre-concentrate comprising a surface active agent, ethanol, and a lipophilic and/or an amphiphilic solvent. Kovacs et al. claims an oral multiple emulsion preconcentrate consisting of a surfactant, ethanol, lipophilic and/or amphiphilic solvent, i.e., active, TPGS, Ethanol, a lipophilic solvent, an amphilic solvent, and a co-tenside. This formulation is claimed to be an improvement over the disadvantages of prior emulsions, i.e., poor stability, development of rancidity, precipitation of the active or excipients, and incompatibility with gelatin films. The colloidal size of the Kovacs et al. microemulsion is said to ensure great specific surface for the transfer into the body fluids. Kovacs et al. also describes other prior art oil-inwater emulsions ex tempore, i.e., mixed by the patient; and a gelatin capsule form wherein an oil-in-water emulsion is formed when the capsule is dissolved, and the oily phase keeps the active drug in what is said to be a dissolved form.

The Eastman Brochure, discloses the use of TPGS as a surface active agent or as an emulsifier, and suggests the blending of TPGS with water and a lipophilic drug to form an oil-in-water emulsion, but does not teach or suggest the direct melt blending of a lipophilic drug, such as cyclosporin, and TPGS to form a solid solution of drug and TPGS.

In sum, the prior art cyclosporine emulsion/microemulsion compositions require multiple component systems. A first hydrophilic solvent component, usually ethanol, is employed as a carrier medium to load the composition with sufficient amounts of cyclosporine and to disperse the drug in second lipophilic component. Surfactants are also required to act as a bridge between the solvent and lipophilic phase, and to inhibit the cyclosporine from precipitating out of the lipophilic phase. In addition, the stabilizing effect of surfactants like castor oil, and solvents like ethanol, is needed to help prevent precipitation of cyclosporine in the gastrointestinal environment. More importantly, these systems cannot be delivered in a controlled fashion. Once the emulsion encounters the GI tract, all of the active is dispersed in order to achieve immediate or rapid absorption.

By contrast, the compositions of the present invention do not require additional surfactants, co-solvents, or ethanol, and can be delivered in a controlled fashion.

Hauer, Antalné, Kovacs, the commercial cyclosporine products, and the Eastman Brochure, all fail to teach or suggest the present invention's direct melt blending and subsequent cooling of a drug and TPGS, or a solvent evaporation technique, in appropriate amounts to form a solid solution of drug and TPGS. Indeed, the prior art references teach away from the present invention in that they disclose complicated systems that seek to solve the cyclosporine solubility problem by adding more and additional non-evaporated co-solvents and surfactants, instead of carefully investigating and utilizing all of the solubility potential of TPGS, when melt blended and cooled with appropriate amounts of drug. Nor does the prior art teach the present invention's method of using liquid crystal formation as a way of obtaining controlled release of the drug.

Other prior art efforts to improve the absorption of cyclosporine also teach away from the present invention. They include co-administration, or concomitant administration, of Vitamin E TPGS and cyclosporine, but again, have failed to investigate whether the direct combination of Vitamin E TPGS with the drug could be achieved.

For example, Sokol et al., *The Lancet*, Vol. 338, 212–215 (1991) discloses oral co-administration of Vitamin E TPGS with cyclosporine to improve the absorption of the drug by pediatric liver transplant patients. Because TPGS was known to be well absorbed in the absence of detectible bile flow, Sokol et al. postulated that TPGS co-administration with cyclosporine might enhance cyclosporine absorption in pediatric transplant patients if poor mixing of bile with cyclosporine or residual cholestasis were causing poor absorption. Similarly, Chang et al., *Clinical Pharmacology & Therapeutics*, Vol. 59, No. 3 (March 1996) discloses the concomitant administration of separate cyclosporine and Vitamin E TPGS dosages in an effort to enhance cyclosporine absorption, and decrease cyclosporine counter transport back into the intestine by P-glycoprotein.

However, neither Sokol et al. nor Chang et al. teach or disclose or teach the combination of TPGS and cyclosporine in single oral dosage form to be administered at one time to the patient. Nor do these references disclose or teach the controlled or sustained release of that dosage.

III. SUMMARY OF THE INVENTION

The present invention dispenses with the prior art's complex cyclosporine emulsion systems and their shortcomings. The prior art follows the conventional, but incorrect, wisdom that the solubilization of cyclosporine could only be enhanced by increasing drug surface area by using surfactants, non-evaporated solvents, co-solvents and granulation agents. Moreover, the objective of the prior art emulsion and micro-emulsion systems was to utilize numerous surfactants and co-solvents to emulsify cyclosporine in a liquid format that would deliver all or most of the cyclosporine dosage to the body at one time. Micro-emulsions are dispersed quickly into the stomach, causing the drug to come quickly out of the emulsion into small particles that will be absorbed in the gut fairly quickly, if not instantly. In the case of cyclosporine, this quick uptake can lead to nephrotoxicity. Therefore, a slower more controlled release is desired.

The solid TPGS/drug composition of the present invention does not require the use of surfactants or non-evaporated co-solvents because the cyclosporine, or other active drug component, is dissolved by melting the drug directly into Vitamin E TPGS, and is then allowed to cool and harden to form a true molecular solid solution. Another useful method uses a solvent to dissolve the drug with TPGS followed by evaporation of solvent to form a true molecular solution—not an emulsion or a micro-emulsion—comprised of a Vitamin E TPGS/drug matrix.

In addition, the new drug TPGS/drug delivery system of the present invention provides a slowly dissolving matrix that absorbs gastrointestinal fluid into the TPGS matrix at the dosage form/fluid interface, where a gel-like liquid crystal is formed. (See FIGS. 1–3). This gel front forms a liquid crystal boundary of a certain thickness or region where drug dissolution is highest. At this liquid crystal/GI fluid boundary a synchronization takes place in which the rate of formation of liquid crystal equals the dissolution rate of liquid crystal at the water interface, thereby giving controlled order release of the drug into the GI tract. In this manner, the rate of dissolution is controlled by both the rate of dissolution of the TPGS liquid crystal formation and the geometry of the dosage form. This leads to controlled release of both dissolved drugs, which are generally lipophillic drugs, or to dispersed drugs, which are generally hydrophilic.

Moreover, unlike the oil-in-water, etc., emulsions of the prior art, the solid Vitamin E TPGS/drug matrix of the present invention can be solidified and then compressed into tablets or caplets, with other excipients, binders and/or fillers. The solid TPGS/drug solution of the present invention also can be made into an immediate release liquid formulation upon addition of water, or into a controlled release system solid tablet by the use of impermeable or semi-permeable barriers or coating surrounding portions of the tablet.

Moreover, the present invention provides drug/Vitamin E TPGS tablet formulations of varied geometries, e.g., circular, cylindrical, triangular, and donut shapes, and which employ impermeable or semi-permeable membranes to aid in controlling the erosion of drug/TPGS matrix in gastric fluid.

V. DESCRIPTION OF SPECIFIC EMBODIMENTS

The Vitamin E TPGS/cyclosporine formulation of the present invention contains from about 0.1 percent to about 20 percent by weight of cyclosporine melt blended together with TPGS in an amount from about 99.9 to about 80 percent by weight TPGS. Other excipients, fillers, binders, disintegrants and lubricants, as described above, may be used to form the composition of the present invention into a tablet, capsule, caplet, parenteral solution, or other dosage form. However, such other excipients may not be added to the TPGS/drug composition in amounts that will cause a significant amount of drug to disassociate itself from the TPGS matrix, thereby inhibiting dissolution or the intended controlled release of the drug. In addition, a solid solution can simply be added to water to provide a immediate release parenteral cyclosporine solution, and does not require the addition of any additional excipients or solvents. However, additional solvents can be added, if desired.

Typically, Vitamin E TPGS and cyclosporine, or other drug component, are combined in a vessel and heated to approximately 45° C. to melt-dissolve the TPGS and drug. In the case of cyclosporine, the melt mixture is held at 45° C. until a clear solution is achieved. If necessary, a higher temperature, up to the decomposition temperature of TPGS or the drug, can be used. The melting point temperature for cyclosporine is about 148° to 151 ° C., about 172° to 174° C. for nifedipine, and about 207.5° to 212° C. for Ditiazem.HCL. Generally, hydrophilic drugs will disperse in the TPGS and will not form a clear solution. However, this does not effect the controlled release of the hydrophilic drug, e.g., Diltiazem.HCl, from the TPGS/drug liquid crystal structure. The melt is cooled until a solid mass is obtained, which can then be processed further.

The TPGS/cyclosporine solid solution can be mixed together with other excipients and compressed into a tablet that will slowly dissolve over its entire surface. Other excipients useful for making a tablet from the Vitamin E TPGS/drug mixture include polyethylene oxide and polymethcrylate copolymers such as POLYOX, a product of Union Carbide, and the EURADIGIT Polymers of Röhm Pharma, GMbH. For example, a melt mixture of 10% cyclosporin and 90% TPGS was cooled and milled together with Polyox WSR-11-5 (Union Carbide) to produce a dry particulate. About 500 mg sample of these particles were compressed on a single 1 cm punch at 1 ton of force. The tablet was added to 100 ml of de-ionized water and dissolved over a 12 hour period.

Other directly compressible binder excipients are also useful for immediate release within the scope of the present invention. Excipients that can be used include DiPac Sugar, sorbitol, mannitol, xylitol, microcrystalline cellulose, Di Tab and mixtures of thereof. This list is not all inclusive, any compressible, flowable material should work. For example, a melt mix of 90:10 TPGS/Astemizole was dry blended at a ratio of 50:50 with 75:25 sorbitol:xylitol. A tablet was made on a single punch using a 1 cm die, 750 mg of tablet mix and 1 ton of force. The tablet when added to 100 ml of 37° C. water started to dissolve immediately. Complete dissolution occurred over a one hour period.

Other excipients to increase the tablet dissolution for instant release tablets include disintegrants usually at 2–4% and include croscarmelose, crospovidone and sodium starch glycolate which are cross-linked cellulose, cross-linked polymer, and cross-linked starch, respectively. Lubricants, glidants, coloring agents and flavors are useful as in traditional tablets. Usually lubricants are used at less than 5%, preferably 1% or less. Glidants are used to improve flow and such materials include silica and talc and are used at 1% or less.

The ability to form tablets from the disclosed invention allows flexibility in the dosage form and in some instances, such as is the case with cyclosporin, it allows the production of a dosage form, e.g., a tablet, which is not possible with the liquid micro-emulsion products now available which must rely on the soft capsule or liquid form.

Conventional tablet mixing and compression techniques, and related equipment, known to those of skill in the art may be used. Tablet mixing and compression methods that may be used with the present invention include wet granulation, fluid bed granulation, dry granulation or direct compression. See Remington's *Pharmaceutical Sciences*, Ch. 89, Mack Publishing (18$^{th}$ Ed. 1990). In addition, tableting equipment and machinery, including single punch machines, and rotary tablet machines, including high speed and multi-layer equipment, can be used, again as described in Remington's, supra.

In the alternative, a capsule can be filled with the TPGS/cyclosporine solution. For example, 000 capsules from Capsugel, a Division of Warner Lambert, may be filled with a drug/TPGS solid solution using conventional capsule filling techniques.

Excipients can be added to the TPGS/drug melt to increase or decrease the delivery rate. Water soluble excipients such as sugar, sorbitol, mannitol, xylitol, sodium carboxy methyl cellulose, hydroxy propyl methyl cellulose and mixtures are useful to increase the rate of dissolution. Hydrophobic materials such as fats and waxes can function to slow the progress of dissolution. Also envisioned for this invention are the use of swellable excipients to either push the water soluble female capsule cap away from the dosage, or, the swellable material could also be added to the bottom of the capsule before filling to aid in the removal of any remaining material in the capsule at the end of use. The swellable material would function by contacting water, and swelling and pushing the remaining undissolved liquid crystal matrix from the capsule into the intestinal tract.

The TPGS/drug can be meted as a hot melt 40° to 50° C. into a gelatin capsule and then cooled in an upright position before ejection from the capsule machine.

Such congealing type capsule machines are available from a number of sources. The preferred machine is supplied by MG Italy and distributed in the USA by MG America. Envisioned are the use of both hard and soft capsules and both manual and automatic capsule filling machines, and methods for use, such as those described in *Remington's Pharmaceutical Sciences*, Mack Publishing, at pp. 1659–1663 (18$^{th}$ Ed. 1990).

Controlled release dosage forms can be prepared by containing the solid drug/Vitamin E TPGS matrix within a water impermeable or semi-permeable barrier or coating having at least one or more openings on the outer surface of the dosage form. Impermeable coating that may be used for this purpose include ethyl cellulose (Ethocell Std. 20) from Dow Chemical Company, and polyvinyl acetate. Semipermeable coatings which may be used include EURADIGIT RS. In addition, acrylic polymers, e.g., the anionic copolymers of methacrylic acid, including those sold under the name EUDRAGIT from Rohm Tech may be used to film coat a portion of the surface of a cyclosporine/Vitamin E TPGS tablet of the present invention.

The coating can be applied by dip coating the bottom half (male portion) of a capsule into a solution of the chosen polymer and air drying the capsule. If necessary, the process can be repeated to obtain the proper coating thickness. The empty male capsules can also be coated using traditional coating equipment like Glatt or Niro fluidized bed coaters. The capsules are added to the coater and sufficient air is added to fluidize the capsules. The polymer is dissolved in either water or organic solvents or mixtures at approximately 10% solids. The choice of solvent and loading level is polymer dependent. The polymer is air sprayed onto the fluidized capsules. Usually the spray rate, air throughput and air temperature are adjusted to maintain a reasonable bed temperature usually around 25°–35° C. Acceptable solvents for the polymers are water for Eudragit RS 30D or acetone/isopropanol for Eudragit RS or RL. These polymers are semipermeable to water.

Tablets can be coated using the same type polymers and solvents described above; however, they are best coated in pan coaters such as Pellegrini, Hicoater or Accela Cota. A useful description of coating procedures and equipment can be found in *Remington's Pharmaceutical Sciences*, Mack Publishing, at pp. 1671–1675 (18$^{th}$ Ed. 1990). In particular, a process for coating dosage forms within the present invention places the tablets into the coater, fluidizes the tablets with drying air at 35°–60° C. The tablets are sprayed with the solvent/polymer at 10% solids at a rate of 2–11 G/min/kg of tablets. Coating is done until the desired film thickness is obtained.

The above description provides a teaching for the use of Vitamin E TPGS as the dissolution control mechanism for either hard-to-dissolve drugs or water soluble drugs. Water insoluble drugs are dissolved in the TPGS matrix. Water soluble drugs are dispersed within the TPGS matrix. It also describes the melt mixing of TPGS with the drug, which is the process necessary for hard-to-dissolve drugs. However, another process dissolves the drug in a solvent with Vitamin E TPGS, and then evaporates the solvent to provide a solid solution. See Example 11, infra. The melt process is also useful, but is not necessary for the formulation of water soluble drugs. Water soluble drugs can also be dry mixed with TPGS and compressed into tablet like slugs which can either be coated or loaded into the capsules as described above. The controlled release still functions in the same way as for the melted form. The structure forms a liquid crystal gel front when it contacts water and slowly dissolves or erodes. As the erosion takes place the water front migrates through the dosage form. Again the rate of erosion controls the dissolution of the drug. And as with the melted form, excipients can be used to aid in tablet formation or to assist in the rate of erosion.

Figure 1:
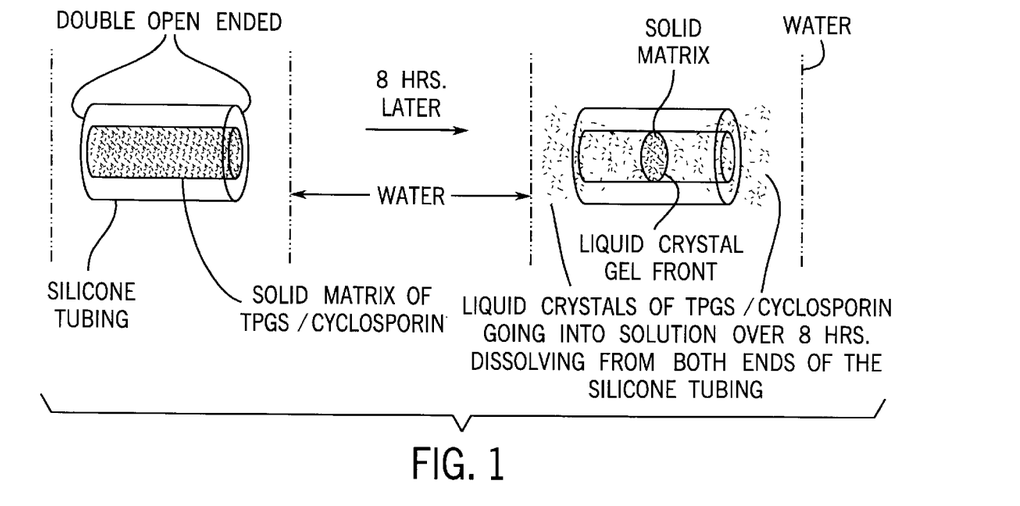
FIG. 1 depicts an open ended cylindrical solid oral dosage form of the present invention, with a water-non-permeable silicone coating around the sides and controlled release of drug product from the ends of the cylinder which are in contact with water or gastrointestinal fluid.

Preferably, only a portion of the tablet should be coated with the impermeable or semi-permeable membrane. This is because the rate of dissolution of the tablet is controlled by both the rate of dissolution of the TPGS liquid crystal formation and the geometry of the dosage form. FIG. 1 illustrates this. FIG. 1 depicts a controlled release device comprising a cylindrical cyclosporine/TPGS solid solution matrix surrounded at its periphery by an impermeable silicone material, but being held open at both ends, which are flat. When placed in solution, the matrix erodes uniformly at both ends towards the mid-point of the cylinder. The silicone prevents water from attacking the cylinder at the side. However at the flat open ends, the water front meets dosage form and forms a slowly eroding liquid crystal/gel front, as depicted in FIG. 3, wherein the drug/TPGS matrix gradually goes into solution at a rate that approaches zero-order kinetics.

In addition to the cylinder geometry of FIG. 1, the present invention includes drug/Vitamin E TPGS tablet and capsule formulations of other geometries, e.g., circular, semi-circular, cylindrical, triangular, rectangular and donut shapes. It will be apparent to those of skill in the art that since the erosion of the drug/Vitamin E TPGS dosage form approaches zero order, the rate of erosion of the entire dosage can be varied by selecting a dosage form configuration from a multitude of geometries and shapes, and coating various portions of the surfaces of that configuration to increase or decrease the rate of erosion. In addition, those of skill in the art will recognize that a given dosage form may employ semi-permeable, instead of impermeable, membranes to vary the rate of the erosion of drug/TPGS matrix in gastric fluid. The effect of variations in geometries and coating areas on the rate of erosion is discussed in U.S. Pat. No. 4,839,177 to Colombo et al., which is incorporated herein by reference.

Some of the zero order release systems, such as the elementary osmotic or the osmotic push/pull systems may be used in conjunction with the present invention. However, it should be noted that these conventional systems do not currently employ TPGS or liquid crystal gel formation. The osmotic system employed by Alza Corp., see U.S. Pat. No. 4,327,725, does use semipermeable polymers to coat the dosage form. This coating controls the influx of water into the dosage. These devices are made by dispersing the active drug ingredient into an appropriate carrier. The present invention would encompass the use of this system wherein the added component is Vitamin E TPGS/drug solid solution. The advantages of the use of TPGS/drug solid solution over the prior art is that what are now considered insoluble drugs can be considered soluble for the purpose of getting the drug out of the osmotic device. This allows formulators greater flexibility in the choice of using the elementary osmotic pump or the more costly and technically difficult push-pull osmotic pump (see U.S. Pat. No. 4,327,725). In this controlled release embodiment, osmotic compounds such as sodium chloride, carbohydrates, or polyethylene glycol are added along with binders and fillers necessary to form a tablet. The tablet is bi-phasic and is made in a two stage tablet press. One phase contains the swellable osmotic component such as polyethylene glycol and the second phase contains the drug mix. Once the tablet is formed it is coated in a pan coater (as described earlier) using semipermeable cellulosics coatings. A hole is then formed into the coated tablet using laser light. This hole permits the outward movement of drug from the tablet. The outward force is supplied by the osmotic pressure of the swellable excipients.

The advantage of the present invention over this prior art is that the Vitamin E TPGS acts both as a good solvent for a number of hard to dissolve drugs but also it will help stabilize the drug once the drug is dispersed inside the coated tablet. This keeps the drug from precipitating or growing crystals so large as to inhibit their exit from the dosage. Hard to dissolve compounds present a real challenge for the osmotic system due to the limited number of excipients that have both water solubility and have solvent properties suitable to dissolve the drug. Our invention improves upon this system because of its solubility and stability enhancement properties.

The stability enhancement properties of TPGS, as used in the present invention, can be seen in Example 8. As shown, even after three months no crystal formation was seen in the Vitamin E TPGS/drug sample. Using control release systems for hard to dissolve drugs is generally considered redundant, pursuant to the conventional thinking in drug formulation development. However, when a drug has toxic side effects such as cyclosporin and others, controlled release becomes necessary. The challenge issued to the formulator is how to control release when the drug itself does not dissolve. The present invention meets that challenge.

The controlled release formulations of the present invention should work in a manner such that other drugs which increase or decrease the blood levels of Neoral and Sandimune cyclosporin formulations will no longer have such an effect when taken with the Vitamin E TPGS/drug formulations. This may occur because Vitamin E TPGS may protect cyclosporine from removal by p-glycoprotein. For example, drugs that enhance blood levels of cyclosporin are calcium channel blockers such as diltiazem, nicardipine, verapamil; antifungals—fluconazole, itraconazole, ketoconazole; antibiotics—clarithromycin, erythromycin; glucocorticoids—methyl prednisolone; allopurihol, bromocriptone, danazol, metoclopramide. Drugs that decrease blood levels of cyclosporin are antibiotics—nafcillin, rifampin; anticonvulsants—barbamazepine, phenobarbital, phenytoin; and others, octreotide and ticlopidine. The present invention is expected to eliminate large blood level fluctuations when the patient is taking other drugs, and is therefore also expected to be a real economic and compliance advantage.

In addition, due to the fact that the present invention provides a TPGS/drug solid dosage form, e.g., a tablet, no refrigeration restrictions are to be expected, in contrast to the commercial NEORAL product. Similarly, the shelf life for the liquid TPGS/drug solutions of the present invention are expected to be greater than that of the current NEORAL product which is about two months after opening the container. (See PHYSICIAN'S DESK REFERENCE, $51^{st}$ Ed. (1997), for NEORAL, p. 2409).

The type of excipients used can affect the rate of erosion. If they are hydrophilic they will generally increase the rate. Lipophilic excipients will generally slow down the release or erosion. The release rate still should approach zero order if the geometry of the dosage is as described above. Hydrophilic excipients will simply increase the rate at which the dosage form will wet and allow the penetration of water, allowing for the controlled erosion of the dosage. On the other hand, lipophilic materials will slow this process by diminishing the wetting of the dosage and slow penetration of water into the form.

It can therefore be seen that the present invention proves wrong the conventional thinking that the solubilization of cyclosporine could only be enhanced by the use of surfactants, solvents, co-solvents and granulation agents in complex systems. The liquid crystal solid TPGS/drug solution of the present invention does not require surfactants or non-evaporated co-solvents because the active drug is dispersed directly into molten Vitamin E TPGS and then allowed to cool and harden to form a true molecular solid solution—not an emulsion or a micro-emulsion—comprised of a Vitamin E TPGS/drug matrix.

In addition, the new drug TPGS/drug delivery system of the present invention provides a slowly dissolving matrix that absorbs gastrointestinal fluid into the TPGS matrix at the dosage form/fluid interface, where a gel-like liquid crystal is formed. (See FIGS. 1, 2 and 3). This gel front forms a liquid crystal boundary of a certain thickness or region where drug dissolution is highest. At this liquid crystal/GI fluid boundary a synchronization takes place in which the rate of formation of liquid crystal equals the dissolution rate of liquid crystal at the water interface, thereby giving controlled release of the drug into the GI tract that approaches zero order.

It is believed that all of these attributes of the present invention can be seen by the following examples, which are intended to illustrate, but not limit, the scope of the invention.

VI. EXAMPLES

Example 1

The objective of this experiment was to examine the solubility enhancement of Vitamin E TPGS alone on an insoluble drug, cyclosporine.

Vitamin E TPGS (d-α-tocopheryl polyethylene glycol 1000 succinate) from Eastman Chemical Co., Kingsport, Tenn., and Cyclosporine from Poli Industria Chimica S.P.A., Italy were used. Eighty-five percent (85%), by weight, of TPGS, and fifteen percent (15%), by weight, of cyclosporine were placed into a 3 gram vial and heated to approximately 45° C. to melt the TPGS. The melt mixture was held at 45° C. until a clear solution was achieved. The above melt was cooled on a bed of ice until a solid mass was obtained. A small amount, approximately 500 mg of the solid mixture was scraped from the vial and then added to 5 ml of water at 35° C.

It was first observed that the TPGS/cyclosporine/water mixture produced a hazy suspension of the TPGS and cyclosporine in the water, and it was not at first believed that a clear solution was achieved. However, the mixture was left intact over night. Upon observation of the vial the next day, the water/TPGS/cyclosporine mixture was clear, and without precipitate, indicating that the cyclosporine was either in a true molecular solution, or in a colloidal solution where the particle size of the cyclosporine was below the human visible range, i.e., below 100 nm, as defined by *Remington's Pharmaceutical Sciences*, 18th Ed., pp. 207, 272 (Mack Publishing Co., Easton, Pa.).

Example 2

The objective of this experiment was to see if that of Example 1 could be repeated with the same results.

The materials, percentages, and methods were the same as those in Example 1. The same results were achieved. Initially, addition of the solid to warm water produced a hazy solution indicating a visible particle size. After 24 hours the hazy suspension was clear and therefore solubilized as in Example 1.

Example 3

The objective of this experiment was to search for the approximate upper and lower limits of solubility of cyclosporine in TPGS when added to water at 35° C.

The materials were the same as in Example 1. Two samples were prepared: Sample A contained 10% cyclosporine in 90% TPGS; Sample B contained 20% cyclosporine in 80% TPGS.

Samples A and B were added to separate 3 gram vials and heated to about 45° to 50° C., and held within that temperature range until a clear solution resulted. Both samples were then cooled in ice until they solidified. 500 mg. from each vial were added to separate vials containing 5 ml of water at 37° C.

The results were that Sample A resulted in a clear solution within one hour with no visible particles when magnified 500× under a light microscope. However, Sample B was still very hazy with unsolubilized drug even after 24 hours. Based on these observations, the upper limit of solubility of a cyclosporine/TPGS melt mixture in water at 37° C., without the use of any co-solvents, surfactants, or other solubility enhancers, appears to be approximately 20 percent. For relatively instant solubility, the concentration of the cyclosporine/TPGS melt mixture in water at 37° C. appears to lie between ten percent and 15 percent, again without the combination of any co-solvents, surfactants, or other solubility enhancers.

Example 4

The objective of this experiment was to determine if the rate of solubility of cyclosporine/TPGS solid solution, containing 90 percent by weight of TPGS, and 10 percent by weight cyclosporine, could be controlled by containing the solid matrix inside a water impermeable cylinder open at both ends.

The materials used were the same as those in Example 1. In addition, Silicon tubing, 7 mm wide and 17 mm in length, was used to serve as non-permeable cylinder. 0.1N HCL was also used.

A cyclosporine/TPGS with a 100 mg cyclosporine dosage was made as follows: 10 percent by weight cyclosporine was melt dissolved in 90 percent by weight TPGS at 50° C. until a clear solution was obtained. This solution was poured, while hot, into the silicone tubing which was stoppered at one end. The stopper was removed after the contents crystallized.

The cylinder, shown in FIG. 1, contained 1 gram of material, i.e., 100 mg of cyclosporine. The cylinder was added to 900 ml. of 0.1N HCL without stirring. The cylinder was observed in the 0.1N HCL over several hours. As shown in FIG. 1, the results showed that dissolution of the solid cyclosporine/TPGS matrix took place over approximately 8 hours and proceeded equally from both ends of the cylinder, indicating that a sustained controlled release of cyclosporine using TPGS alone as the carrier excipient for poorly soluble materials was feasible.

Example 5

The objective of this experiment was to examine if coating the inside and part of the outside of a capsule with Ethocell, without coating the top outside of the cap will permit release of cyclosporine from the TPGS matrix.

The materials used were the same as those in Example 1. In addition, 000 capsules from Capsugel, a Division of Warner Lambert, ethyl cellulose (Ethocell Std. 20) from Dow Chemical Company, and undenatured ethanol 200 proof was used.

A solution of 10% Ethocell was made using ethanol as the solvent. The solution was made by addition of Ethocell to ethanol over 10 minutes while stirring the ethanol. The solution was allowed to stand overnight to insure complete solubility of the polymer. Ten percent by weight cyclosporine was dissolved, as described above, in 90% TPGS at 50 degrees C until a clear solution was obtained. The capsules were dipped coated into the Ethocell solution several times, taking care to leave the top part of the capsule uncoated. The capsules were dried overnight. Two capsule parts were filled as follows: Sample A contained one gram of the TPGS/cyclosporine solution; Sample B contained 1.1 gram of the TPGS/cyclosporine solution. The solutions were added to the capsules when hot. The top parts (uncoated) were placed on the capsules and the capsules were allowed to solidify overnight. The capsules were placed in a dissolution apparatus at 37° C. and 75 rpm using 900 ml dionized water. The samples were observed over an 8 hour period.

Figure 2:
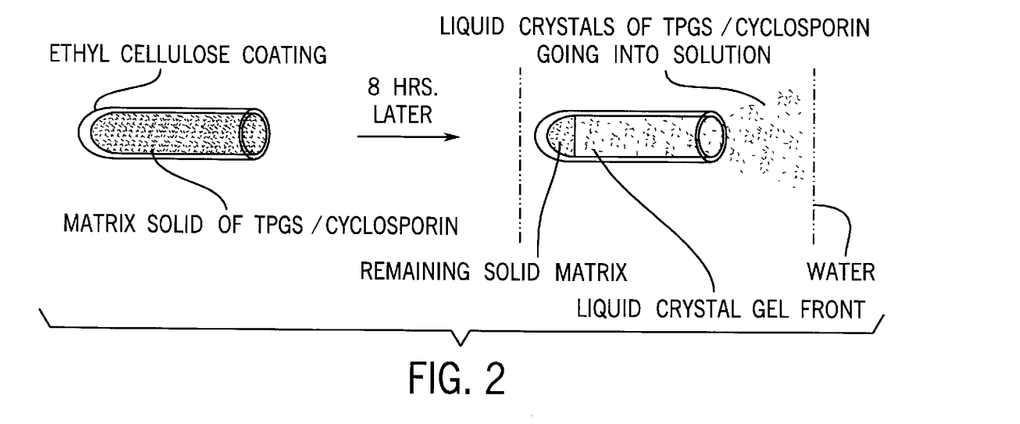
FIG. 2 shows a capsule containing a Vitamin E TPGS/cyclosporine solid solution of the present invention wherein one end of the capsule has a non-permeable ethyl cellulose coating, thereby permitting the release of the water soluble cap at the other end, and subsequent controlled release of cyclosporine from within the capsule by slow dissolution of the internal matrix from the open end exposed to water.

As shown in FIG. 2, The results obtained showed that the capsules containing 1 gram of TPGS/cyclosporine were dissolved over the 8 hour period, whereas the capsule that contained 1.1 gram of TPGS/cyclosporine had 20% of that product remaining. By coating of the capsules with Ethocell, yet without placing the Ethocell coating on the top, water soluble, part of the capsule appeared to allow the release of the water soluble cap and therefore the controlled release of the cyclosporine from the solid matrix by slow dissolution of the matrix from the open end of the capsule, which was exposed to the water front.

Example 6

The objective of this experiment was to test the reproducibility of the in vitro dissolution testing of one gram of TPGS/cyclosporine 000 capsules of the present invention.

The materials used were the same as in Example 1. The male parts of the capsules were coated as in Example 5. A solution of 10% cyclosporine in 90% TPGS was prepared by melting the compounds together and holding the solution at 50° C. until a clear melt solution was obtained. One gram of the hot solution was pipetted into three of the above coated capsules. After placing the top water soluble cap into place, the capsules were held overnight to solidify the mass. The capsules were then added to 900 ml of dionized water at 37° C. and stirred at 100 rpm. The water soluable caps had dissolved. The remaining male parts of the capsules were removed after 10 hours and dried for one week at room temperature. The remaining solid was removed from the capsule parts and weighed.

The results obtained showed that the delivery of the drug in dionized water was 77.7% to 88.6%, indicating reasonable reproducibility of the delivery.

Example 7

The objective of this experiment was to determine if other drugs, both water soluble and water insoluble drugs, can be delivered in a controlled sustained fashion using TPGS as the delivery matrix.

The materials used were the same as Examples 1 and 4. In addition, Diltiazem.HCL (water soluble) was obtained from ABIC, Netanya, Israel, and Nifedipine (water insoluble) was obtained from Moehs S. A.

0.7 g of Nifedipine was added to 2.7 grams of TPGS (20% by weight). The mixture was heated to approximately 100° C. to obtain a clear solution. A second sample, 20% loading by weight, was made using Diltiazem.HCl.

While hot and fluid, both samples were added to separate pieces of silicone tubing (7 mm×16 mm long) before cooling and solidifying at room temperature. The next day both samples were added to 200 ml of warm water and observed without stirring over time.

The results obtained showed that both samples dissolved over a 6 to 8 hour period uniformly from each end of the two open ended cylinders. This indicated that the TPGS matrix is useful as a control release system for both water soluble and water insoluble drugs.

Example 8

The objective of this experiment was to test the stability of the commercial Cyclosporine emulsion product of the prior art, i.e., NEORAL by Sandoz, against the TPGS/cyclosporine solutions of the present invention.

The materials of the present invention were the same as in Example 1. In addition, NEORAL from Sandoz (capsules containing 10% by weight of cyclosporine) were obtained.

One gram of the NEORAL capsule fluid containing 100 mg of cyclosporine was added to 5 ml of water. One gram of the TPGS/cyclosporine (10%), solid matrix, prepared as in the previous examples above and containing 100 mg of Cyclosporine was also added to 5 ml of water. The samples were held at room temperature for three months and the observed under a microscope.

The results obtained showed that the Neoral sample was very hazy and contained large crystals of about 500 um (microns) as seen with an Olympus (Opolco Optical Elements Corp.) stereo compound microscope using a 225× magnification with polarizer in place. By contrast, the TPGS sample was crystal clear and had no crystal growth as seen by the microscope at 225×. These results indicated that the TPGS/cyclosporine of the present invention results in a surprisingly stable product, much more stable than the current product on the market, NEORAL.

Example 9

The objective of this experiment was to determine if water soluble drugs affect the erosion rate of the TPGS capsule dosage.

The materials used were ticlopidine salt (a water soluble compound) and oxaprozin (a water insoluble compound), both from Interchem USA, double zero capsules coated as in Examples 5, 6 and 10, male part only, water soluble female part caps, and TPGS (from Eastman Chemical Co., Kingsport, Tenn.).

Ten percent by weight of ticlopidine was melt blended with TPGS until all of the TPGS/drug was melted to form a free flowing liquid. Ten percent by weight of Oxaprozin was melt blended with TPGS until a clear melt was observed. Then, one gram of each the melted drug/TPGS solution was placed into the male part of the 00 capsules. The liquid was allowed to crystallize in the capsule before capping with the female part. This was allowed to set overnight (24 hrs), and was then added to 200 ml of water. After about 8 hours, approximately 33% of the drug/TPGS matrix of each sample remained in each of the capsule.

Based on this observation, it was concluded that the presence of water soluble drugs over water insoluble drugs has little to no effect on the rate of erosion of the dosage form.

Example 10

The objective of this experiment was to determine if the semipermeable polymer Eudragit RS could be used to coat gelatin capsule formulations of the present invention.

The materials used were 000 capsules (from Capsugel), TPGS (from Eastman Chemical Co., TN), Eudragit RS (from Rohm Tech), Acetone (from Aldrich Chemical), Triethyl Citrate (from Morfiex Inc.) and Cyclosporin (from Interchem Inc.).

The method used was as follows: Eudragit RS, 10% by weight, was dissolved in acetone, 89.5% by weight, and 0.5% Triethyl Citrate by weight. The capsule bottoms (male parts) were then dip coated 5 times, coating up to the lip of the capsule, in this solution. The capsules were then dried with an air gun between each coating. The capsules were then dried upside down over 24 hours and then filled with 1 gram of molten TPGS/Cyclosporin (90:10). The filled capsules were cooled and the TPGS crystallized before placing the female water soluble top cap in place. The samples were held for 24 hours before adding to 100 ml of de-ionized water. The capsules were left unstirred for 10 hours.

It was observed, at the end of the ten hour period, that the capsules were empty. The contents of the capsules eroded uniformly over time. The capsule coating appeared to be useful as a coating for the protection of the TPGS contents. It was concluded that the semipermeable polymer Eudragit RS is a useful coating for a gelatin capsule and functions to hold the contents of a capsule in place and permit erosion from the open end of the capsule.

Example 11

The objective of this experiment was to determine whether a solvent evaporation process will work to dissolve a hard to dissolve drug with Vitamin E TPGS.

The materials used were Cyclosporine from Poli Industria Chimica S.P.A., Italy; ethyl alcohol, 200 proof, from Warner-Graham Co., Cockeysville, Maryland; Vitamin E TPGS from Eastman Chemical Co., Kingsport, Tenn.

200 mg of Cyclosporine was weighed into a 100 ml beaker and 1.2 grams of Vitamin E TPGS was added, and to this was added 8 grams of ethanol. The ethanol solvent, Cyclosporine, and TPGS were stirred at room temperature for 10 minutes until the Cyclosporine and TPGS components were clearly dissolved. The solvent was evaporated from a Petri dish overnight and the sample was examined under an Olympus BX50 microscope at 200× magnification by adding a small quantity of water to the cyclosporine/TPGS, and watching for visible crystals. No crystals were observed, only a clear solution was obtained. It was therefore concluded that solvent evaporation will also work to produce clear solutions of Cyclosporine/TPGS when added to water.

I claim:

1. A pharmaceutical composition comprising:
   a) Vitamin E TPGS in an amount of 50 to 99.9% by weight; and
   b) one or more active lipophilic drug components in an amount from 0.1 to 50% by weight;
wherein at least one of the active drug components is in solid solution with the Vitamin E TPGS without co-solvents or surfactants.

2. A pharmaceutical composition comprising:
   a) Vitamin E TPGS in an amount of 50 to 99.9% by weight; and
   b) one or more active hydrophilic drug components in an amount from 0.1 to 50% by weight;
wherein at least one of the active drug components is in a solid dispersion with the Vitamin E TPGS without co-solvents or surfactants.

3. A pharmaceutical composition in solid form comprising:
   a) Vitamin E TPGS in an amount of 50 to 99.9% by weight; and
   b) one or more other active drug components in an amount from 0.1 to 50% by weight;
wherein at least one of the active drug components is in a solid solution with the Vitamin E TPGS without co-solvents or surfactants.

4. A pharmaceutical composition of claim 3 wherein the pharmaceutical composition is in the form of a capsule.

5. An oral solid pharmaceutical dosage form comprising:
   a) Vitamin E TPGS in an amount of 1 to 50% by weight;
   b) one or more other active drug components in an amount of 0.1 to 30% by weight;
   c) a binder in an amount of 1 to 99% by weight; and
   d) a filler in an amount of zero to 85% by weight;
wherein at least one of the active drug components is in solid solution with Vitamin E TPGS without co-solvents or surfactants.

6. A pharmaceutical composition comprising:
   a) Vitamin E TPGS in an amount of 80 to 99.9% by weight; and
   b) a cyclosporin in an amount from 0.1 to 20% by weight;
wherein the cyclosporin is in solid solution with Vitamin E TPGS without co-solvents or surfactants.

7. A pharmaceutical composition comprising:
   a) Vitamin E TPGS in an amount of 80 to 99.9% by weight; and
   b) nifedipine in an amount from 0.1 to 20% by weight;
wherein the nifedipine is in solid solution with Vitamin E TPGS without co-solvents or surfactants.

8. A pharmaceutical composition comprising:
   a) Vitamin E TPGS in an amount of 80 to 99.9% by weight; and
   b) diltiazem.HCl in an amount from 0.1 to 20% by weight; wherein the diltiazem.HCl is in a solid dispersion with the Vitamin E TPGS without co-solvents or surfactants.

9. A controlled release solid pharmaceutical composition dosage form comprising:
   a) Vitamin E TPGS and active drug component in solid solution or dispersion with said Vitamin E TPGS without co-solvents or surfactants; and
   b) at least one coating comprising a pharmaceutically acceptable polymer covering at least a portion of said dosage form.

10. The controlled release pharmaceutical composition of claim 9 wherein the active drug component is a cyclosporin.

11. The controlled release pharmaceutical composition of claim 9 wherein the active drug component is nifedipine.

12. The controlled release pharmaceutical composition of claim 9 wherein the active drug component is diltiazem.HCl.

13. The controlled release pharmaceutical composition of claim 9 wherein the pharmaceutical composition is in the form of an oral dosage.

14. The controlled release pharmaceutical composition of claim 9 wherein the pharmaceutical composition is in the form of a tablet.

15. The controlled release pharmaceutical composition of claim 9 wherein the pharmaceutical composition is in the form of a capsule.

16. The controlled release pharmaceutical composition of claim 9 wherein the coating is at least partially impermeable.

17. The controlled release pharmaceutical composition of claim 9 wherein the coating is at least partially semi-permeable.

18. The controlled release pharmaceutical composition of claim 14 wherein said coating has at least a partially impermeable barrier to water around at least part of the tablet.

19. A method of making a lipophilic drug composition with enhanced aqueous solubility comprising:
   a) combining said lipophilic drug together with Vitamin E TPGS without co-solvents or surfactants to form a liquid solution comprising the drug and Vitamin E TPGS; and
   b) cooling said liquid solution to form a solid composition comprising the drug and Vitamin E TPGS.

20. A method of making a cyclosporin composition with enhanced aqueous solubility comprising:
   a) combining between 0.1 to 20% by weight of cyclosporin together with Vitamin E TPGS without co-solvents or surfactants to form a liquid solution comprising a cyclosporin and Vitamin E TPGS; and b) cooling said liquid solution to form a solid solution comprising Vitamin E TPGS and 0.1 to 20% by weight of the cyclosporin.

21. A method of making a nifedipine composition with enhanced aqueous solubility comprising:
   a) combining between 0.1 to 50% by weight of nifedipine together with Vitamin E TPGS without co-solvents or surfactants to form a liquid solution comprising nifedipine and Vitamin E TPGS; and
   b) cooling said liquid solution to form a solid solution comprising Vitamin E TPGS and 0.1 to 50% by weight of nifedipine.

22. A method of making an oral pharmaceutical dosage form comprising:
   a) combining a drug together with Vitamin E TPGS without co-solvents or surfactants to form a liquid dispersion comprising the drug and Vitamin E TPGS;
   b) cooling said liquid dispersion to form a solid composition comprising the drug and Vitamin E TPGS;
   c) mixing said drug and Vitamin E TPGS composition; and
   d) filling a capsule with said composition.

23. The method of claim 22 further comprising adding a filler to the drug/Vitamin E TPGS composition after the mixing step.

24. A method of preparing a oral solid pharmaceutical dosage form comprising:
   a) combining a drug together with Vitamin E TPGS without co-solvents or surfactants to form a liquid solution comprising the drug and Vitamin E TPGS;
   b) cooling said liquid solution to form a solid composition comprising the drug and Vitamin E TPGS;
   c) mixing said drug and Vitamin E TPGS composition together with a binder to form a mixture thereof; and
   d) compressing said mixture into a tablet.

25. The controlled release pharmaceutical composition of claim 9 comprising a partially impermeable coating and a partially semi-permeable coating.

26. A pharmaceutical composition comprising a solid solution, said solid solution consisting essentially of Vitamin E TPGS and one or more active drug components.

27. The pharmaceutical composition of claim 26, wherein said active drug component is a lipophilic drug component and is present in said solid solution in an amount of from 0.1 to 50% by weight.

28. A pharmaceutical composition comprising a solid dispersion, said solid dispersion consisting essentially of Vitamin E TPGS and one or more active hydrophilic drug components.

29. The pharmaceutical composition of claim 27, wherein said lipophilic drug component is selected from the group consisting of immnunosuppressants.

30. The pharmaceutical composition of claim 29, wherein said immunosuppressant is at least one member selected from the group consisting of cyclosporins.

31. The pharmaceutical composition of claim 30, wherein said cyclosporin is Cyclosporin A.

32. The pharmaceutical composition of claim 30, wherein said cyclosporin is present in an amount of from 0.1 to 20% by weight.

33. The pharmaceutical composition of claim 26, wherein said active drug component is at least one member selected from the group consisting of calcium antagonists.

34. The pharmaceutical composition of claim 33, wherein said calcium antagonist is present in an amount of from 0.1 to 50% by weight.

35. The pharmaceutical composition of claim 33, wherein said calcium antagonist is nifedipine.

36. The pharmaceutical composition of claim 35, wherein said nifedipine is present in an amount of from 0.1 to 20% by weight.

37. The pharmaceutical composition of claim 28, wherein said active drug component is at least one member selected from the group consisting of calcium antagonists.

38. The pharmaceutical composition of claim 37, wherein said active drug component is present in an amount of from 0.1 to 50% by weight.

39. The pharmaceutical composition of claim 38, wherein said active drug component is diltiazem.

40. The pharmaceutical composition of claim 39, wherein said diltiazem is present in an amount of from 0.1 to 20% by weight.

41. A method of forming a pharmaceutical composition, comprising forming a solid solution consisting essentially of Vitamin E TPGS and at least one member selected from the group consisting of active drug components.

* * * * *